(12) United States Patent
Spelberg et al.

(10) Patent No.: US 11,053,518 B2
(45) Date of Patent: Jul. 6, 2021

(54) METHOD FOR THE PREPARATION OF CHIRAL ALPHA HALOALKANOIC ACIDS

(71) Applicant: Bayer Aktiengesellschaft, Leverkusen (DE)

(72) Inventors: Markus Spelberg, Duesseldorf (DE); Julian Egger, Remscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 16/650,311

(22) PCT Filed: Sep. 24, 2018

(86) PCT No.: PCT/EP2018/075752
§ 371 (c)(1),
(2) Date: Mar. 24, 2020

(87) PCT Pub. No.: WO2019/063463
PCT Pub. Date: Apr. 4, 2019

(65) Prior Publication Data
US 2020/0277633 A1 Sep. 3, 2020

(30) Foreign Application Priority Data
Sep. 28, 2017 (EP) .................................. 17193736

(51) Int. Cl.
*C12P 7/40* (2006.01)
*C12P 41/00* (2006.01)

(52) U.S. Cl.
CPC .................. *C12P 7/40* (2013.01); *C12P 41/00* (2013.01)

(58) Field of Classification Search
CPC ........... C12P 7/40; C12P 41/00; C12P 41/002; C12Y 308/01002
See application file for complete search history.

(56) References Cited

U.S. PATENT DOCUMENTS

| 4,758,518 | A | * | 7/1988 | Taylor | C12P 7/56 435/195 |
|---|---|---|---|---|---|
| 5,154,738 | A | | 10/1992 | Armstrong | |

FOREIGN PATENT DOCUMENTS

| CN | 103509778 | * | 1/2014 | ............ C12N 9/14 |
|---|---|---|---|---|
| CN | 103509778 | B | 4/2016 | |
| EP | 0179603 | A2 | 4/1986 | |
| JP | S5931690 | A | 2/1984 | |

OTHER PUBLICATIONS

Goldman P. The enzymatic cleavage of the carbon-fluorine bond in fluoroacetate. The J. Biol. Chem., 1965, vol. 240(8): 3434-3438. (Year: 1965).*
Goldman P. Carbon-halogen bond cleavage. The J. Biol. Chem., 1968, vol. 243(2): 428-434. (Year: 1968).*
Janssen et al., Approaches for Bioremediation of Organic Pollution; edited by Fass et al., Kluwer Academic/Plenum Publishers, New York, 1999, pp. 105-116 (Year: 1999).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
International Search Report for Application No. PCT/EP2018/075752 dated Mar. 28, 2019.
Tatsuo Kurihara and Nobuyoshi Esaki, "Bacterial Hydrolytic Dehalogenases and Related Enzymes: Occurrences, Reaction Mechanisms, and Applications," The Chemical Record, (2008), vol. 8, 67-74.
Philip G. Bachas-Daunert, et al., "Characterization of a Recombinant Thermostable Dehalogenase Isolated from the Hot Spring Thermophile Sulfolobus tokodaii," Applied Biochemistry and Biotechnology (2009), 159:382-393.
David A. H. Jones, et al., "Nucleotide sequence of the structural gene encoding a 2-haloalkanoic acid dehalogenase of Pseudomonas putida strain AJ1 and purification of the encoded protein," Journal of General Microbiology, (1992) vol. 138, 675-683.
Carrie A. Rye, et al., "Biochemical and structural studies of a L-haloacid dehalogenase from the thermophilic archaeon Sulfolobus tokodaii," Extremophiles, (2009) 13:179-190.
Kenzo Motosugi, et al., "Purification and Properties of 2-Halo Acid Dehalogenase from Psueudomonas putida," Agricultural and Biological Chemistry, (1982) vol. 46, No. 3:837-838.
Melvin Little and Peter A. Williams, "A Bacterial Halidohydrolase: Its Purification, Some Properties and its Modification by Specific Amino Acid Reagents," European Journal of Biochemistry (1971), vol. 21, No. 1:99-109.
Database UniProt [Online] Aug. 30, 2017, RecName Full=(S)-2-haloacid dehalogenase H-109; EC=3.8.1.2; Pseudomonas putida No. 109; entry version 67., Database accession No. Q59728.
Database UniProt [Online] Aug. 30, 2017, RecName Full=(S)-2-haloacid dehalogenase; EC=3.8.1.2; Entry version 65., Database accession No. Q59666.

* cited by examiner

Primary Examiner — Ganapathirama Raghu
(74) Attorney, Agent, or Firm — McBee Moore & Vanik IP, LLC

(57) ABSTRACT

What is described herein relates to a method of selectively hydrolyzing an enantiomer of an alpha haloalkanoic acid according to formula I employing a polypeptide having dehalogenase activity comprising an amino acid sequence as set forth in SEQ ID NO. 1 or SEQ ID NO. 4 or a sequence with at least 80% sequence identity to either of said sequences and to the use of said method.

13 Claims, 5 Drawing Sheets
Specification includes a Sequence Listing.

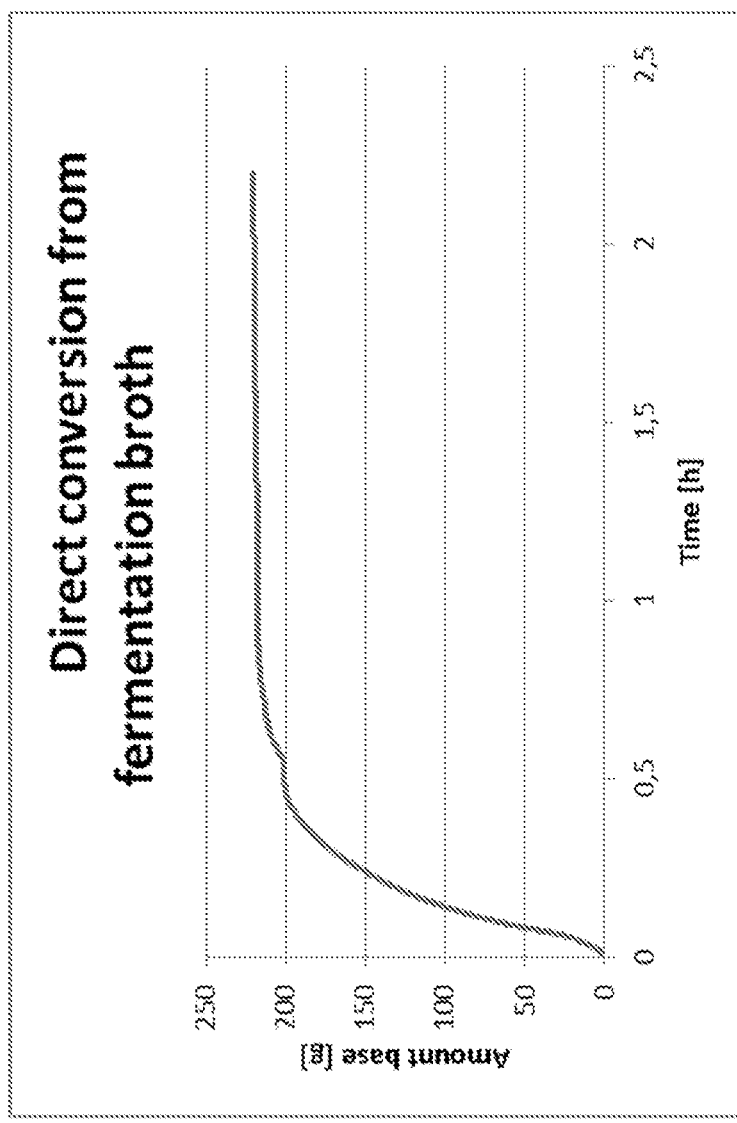

SEQUENCE LISTING

<160> NUMBER OF SEQ ID NOS: 8

<210> SEQ ID NO 1
<211> LENGTH: 227
<212> TYPE: PRT
<213> ORGANISM: Pseudomonas putida

<400> SEQUENCE: 1

Met Lys Asn Ile Gln Gly Ile Val Phe Asp Leu Tyr Gly Thr Leu Tyr
1               5                   10                  15

Asp Val His Ser Val Val Gln Ala Cys Glu Glu Val Tyr Pro Gly Gln
            20                  25                  30

Gly Asp Ala Ile Ser Arg Leu Trp Arg Gln Lys Gln Leu Glu Tyr Thr
        35                  40                  45

Trp Leu Arg Ser Leu Met Gly Arg Tyr Val Asn Phe Glu Lys Ala Thr
50                  55                  60

Glu Asp Ala Leu Arg Phe Thr Cys Thr His Leu Gly Leu Ser Leu Asp
65                  70                  75                  80

Asp Glu Thr His Gln Arg Leu Ser Asp Ala Tyr Leu His Leu Thr Pro
                85                  90                  95

Tyr Ala Asp Thr Ala Asp Ala Val Arg Arg Leu Lys Ala Ala Gly Leu
                100                 105                 110

Pro Leu Gly Ile Ile Ser Asn Gly Ser His Cys Ser Ile Glu Gln Val
        115                 120                 125

Val Thr Asn Ser Glu Met Asn Trp Ala Phe Asp Gln Leu Ile Ser Val
130                 135                 140

Glu Asp Val Gln Val Phe Lys Pro Asp Ser Arg Val Tyr Ser Leu Ala
145                 150                 155                 160

Glu Lys Arg Met Gly Phe Pro Lys Glu Asn Ile Leu Phe Val Ser Ser
                165                 170                 175

Asn Ala Trp Asp Ala Ser Ala Ala Ser Asn Phe Gly Phe Pro Val Cys
                180                 185                 190

Trp Ile Asn Arg Gln Asn Gly Ala Phe Asp Glu Leu Asp Ala Lys Pro
            195                 200                 205

Thr His Val Val Arg Asn Leu Ala Glu Met Ser Asn Trp Leu Val Asn
        210                 215                 220

Ser Leu Asp
225

<210> SEQ ID NO 2
<211> LENGTH: 684
<212> TYPE: DNA
<213> ORGANISM: Pseudomonas putida

<400> SEQUENCE: 2
atgaagaaca ttcagggcat tgtgtttgac ctctatggta cgctgtatga cgtacacagc      60
gtcgttcaag cgtgtgaaga agtttaccct ggtcaaggcg atgcgatttc ccgtttgtgg     120
cgtcagaaac agctggaata cacgtggttg cgttccttga tgggacgcta tgtcaacttc     180
gagaaagcga ctgaggatgc gttacgcttt acctgtacgc acctgggtct gtcccttgac     240
gacgaaaccc atcaacgtct gagcgatgcc tatctccacc tgactccgta cgcagataca     300
gccgatgcag ttcgtcggtt aaaagccgca ggcttaccac tggggatcat cagcaatggc     360
agtcattgca gcattgaaca ggtggtaacc aactcggaaa tgaactgggc tttcgatcag     420
ctgatttcgg tcgaagatgt ccaggtgttc aaacccgatt ctcgcgtgta ttcactggcg     480
gagaaacgca tgggctttcc gaaggagaac atcctcttcg tgagttcgaa tgcttgggat     540
gcgtcagctg cctctaactt tgggtttccg gtttgctgga tcaatcgcca gaatggtgcg     600
tttgacgaac tggatgccaa accgacccat gtggtacgca atctggcaga aatgagcaat     660
tggcttgtga acagtctgga ctaa                                            684

```
<210> SEQ ID NO 3
<211> LENGTH: 684
<212> TYPE: DNA
<213> ORGANISM: Pseudomonas putida

<400> SEQUENCE: 3
atgaaaaaca tccaaggtat cgttttcgat ttgtatggca cgctctacga cgtgcattcc     60
gtggtgcaag cctgtgaaga ggtctatccg ggccaaggcg acgctatttc tcgcctctgg    120
cggcaaaagc aattggaata cacctggctc aggagcctca tgggccgtta cgtgaacttt    180
gagaaagcaa cagaggatgc cttgcgcttt acctgcacgc atctgggctt gtcgctcgat    240
gatgaaaccc accagcgcct cagtgatgct tatttgcacc tcaccccta tgccgataca     300 gctgacgccg ttcgccgttt gaaagctgcg ggcctaccgc taggcatcat ttcaaatggt    360
tctcattgct cgatcgagca agtcgtgact aactctgaaa tgaattgggc gttcgatcag    420
ctgatcagcg tcgaggatgt gcaagtgttc aaacctgata gtcgcgtcta tagccttgcc    480
gagaagcgca tgggttttcc aaaggaaaac atcctcttcg tttcgtcaaa cgcgtgggat    540
gcgagtgcag ccagtaactt tggtttcccg gtttgctgga tcaatcggca gaacggcgcg    600
tttgatgagc tggatgcaaa gccgacacac gtcgtgcgta atctcgccga aatgtcgaac    660
tggctggtta attcgctcga ttaa                                           684

<210> SEQ ID NO 4
<211> LENGTH: 201
<212> TYPE: PRT
<213> ORGANISM: Sulfolobus tokodaii

<400> SEQUENCE: 4

Met Ile Ile Leu Ala Phe Asp Ile Phe Gly Thr Val Leu Asp Thr Ser
1               5                   10                  15

Thr Val Ile Gln Glu Phe Arg Asn Lys Gln Leu Glu Tyr Thr Trp Leu
            20                  25                  30

Leu Thr Ile Met Gly Lys Tyr Val Glu Phe Glu Glu Ile Thr Lys Ile
        35                  40                  45

Thr Leu Arg Tyr Ile Leu Lys Val Arg Gly Glu Glu Ser Lys Phe Asp
    50                  55                  60

Glu Glu Leu Asn Lys Trp Lys Asn Leu Lys Ala Tyr Glu Asp Thr Lys
65                  70                  75                  80

Tyr Leu Lys Glu Ile Ser Glu Ile Ala Glu Val Tyr Ala Leu Ser Asn
                85                  90                  95

Gly Ser Ile Asn Glu Val Lys Gln His Leu Glu Arg Asn Gly Leu Leu
            100                 105                 110

Arg Tyr Phe Lys Gly Ile Phe Ser Ala Glu Ser Val Lys Glu Tyr Lys
        115                 120                 125

Pro Ser Pro Lys Val Tyr Lys Tyr Phe Leu Asp Ser Ile Gly Ala Lys
    130                 135                 140

Glu Ala Phe Leu Val Ser Ser Asn Ala Phe Asp Val Ile Gly Ala Lys
145                 150                 155                 160

Asn Ala Gly Met Arg Ser Ile Phe Val Asn Arg Lys Asn Thr Ile Val
                165                 170                 175

Asp Pro Ile Gly Gly Lys Pro Asp Val Ile Val Asn Asp Phe Lys Glu
            180                 185                 190

Leu Tyr Glu Trp Ile Leu Arg Tyr Lys
        195                 200
```

<210> SEQ ID NO 5
<211> LENGTH: 606
<212> TYPE: DNA
<213> ORGANISM: Sulfolobus tokodaii

<400> SEQUENCE: 5

| | | | | | |
|---|---|---|---|---|---|
| atgatcattc | tggcctttga | tatctttggt | actgtactcg | atacatctac | cgttatccag | 60 |
| gaatttcgca | acaaacaact | ggagtatact | tggctgctga | cgattatggg | caaatacgtg | 120 |
| gaatttgagg | aaatcaccaa | aattacgtta | cgctatatcc | tgaaagttcg | tggtgaagaa | 180 |
| tcgaagtttg | acgaagaact | gaacaaatgg | aagaacctga | agcgtatga | agataccaaa | 240 |
| taccttaaag | agatttcgga | aattgccgaa | gtttatgcgc | tgtcaaatgg | gagtattaac | 300 |
| gaagtgaaac | agcatttgga | acgtaatggg | ttacttcggt | acttcaaagg | catttcctcc | 360 |
| gcagaaagcg | ttaaagagta | caaaccgagt | ccgaaagtgt | ataagtactt | tctggatagc | 420 |
| attggtgcga | agaagccctt | cttggtatct | agcaacgcat | tcgatgtgat | tggcgctaag | 480 |
| aatgctggta | tgcgttccat | ctttgtcaat | cgcaagaaca | ccattgtcga | tcctatcggc | 540 |
| ggaaaaccag | acgtgatcgt | caatgacttc | aaagagctgt | atgagtggat | tctccgctat | 600 |
| aaataa | | | | | 606 |

<210> SEQ ID NO 6
<211> LENGTH: 606
<212> TYPE: DNA
<213> ORGANISM: Sulfolobus tokodaii

<400> SEQUENCE: 6

| | | | | | |
|---|---|---|---|---|---|
| atgatcattc | tagcatttga | tatcttcgga | acagttcttg | atacatctac | ggtaattcaa | 60 |
| gagtttagga | ataagcaatt | agagtataca | tggttactta | caataatggg | gaaatatgtg | 120 |
| gaatttgagg | aaataacaaa | gattacttta | agatacatct | taaaggtaag | aggcgaagag | 180 |
| agcaaatttg | atgaggagtt | aaataagtgg | aagaatctta | agcttatga | agatactaaa | 240 |
| tatttaaagg | aaatatctga | gatagccgag | gtctacgcgt | tatctaacgg | gtctataaat | 300 |
| gaggttaaac | aacatttaga | gcgcaatggt | ttgttaagat | attttaaggg | catatttagt | 360 |
| gcagaaagtg | ttaaagaata | taaaccttca | cctaaagtat | acaaatattt | cctagactcg | 420 |
| ataggagcta | agaagcatt | cttagtttca | tcaaatgcat | ttgacgtcat | aggagctaaa | 480 |
| aacgcgggta | tgaggagtat | attcgtaaat | aggaagaata | caatagtcga | tcctataggt | 540 |
| ggcaaacctg | atgttatagt | aaatgacttc | aaagagttat | atgaatggat | tttgcgatat | 600 |
| aagtga | | | | | 606 |

<210> SEQ ID NO 7
<211> LENGTH: 4515
<212> TYPE: DNA
<213> ORGANISM: Artificial Sequence
<220> FEATURE:
<223> OTHER INFORMATION: pKA81a-HADH-PP-AJ plasmid

<400> SEQUENCE: 7

| | | | | | |
|---|---|---|---|---|---|
| ttagaaaaac | tcatcgagca | tcaaatgaaa | ctgcaattta | ttcatatcag | gattatcaat | 60 |
| accatatttt | tgaaaagcc | gtttctgtaa | tgaaggagaa | aactcaccga | ggcagttcca | 120 |
| taggatggca | agatcctggt | atcggtctgc | gattccgact | cgtccaacat | caatacaacc | 180 |
| tattaatttc | ccctcgtcaa | aaataaggtt | atcaagtgag | aaatcaccat | gagtgacgac | 240 |
| tgaatccggt | gagaatggca | aaagtttatg | catttctttc | cagacttgtt | caacaggcca | 300 |

```
gccattacgc tcgtcatcaa aatcactcgc atcaaccaaa ccgttattca ttcgtgattg      360
cgcctgagcg agacgaaata cgcgatcgct gttaaaagga caattacaaa caggaatcga      420
atgcaaccgg cgcaggaaca ctgccagcgc atcaacaata ttttcacctg aatcaggata      480
ttcttctaat acctggaatg ctgtttccc ggggatcgca gtggtgagta accatgcatc       540
atcaggagta cggataaaat gcttgatggt cggaagaggc ataaattccg tcagccagtt      600
tagtctgacc atctcatctg taacatcatt ggcaacgcta cctttgccat gtttcagaaa      660
caactctggc gcatcgggct tcccatacaa tcgatagatt gtcgcacctg attgcccgac      720
attatcgcga gcccatttat acccatataa atcagcatcc atgttggaat ttaatcgcgg      780
cctagagcaa gacgtttccc gttgaatatg gctcataaca ccccttgtat tactgtttat      840
gtaagcagac agttttattg ttcatgacca aaatccctta acgtgagttt tcgttccact      900
gagcgtcaga ccccgtagaa aagatcaaag gatcttcttg agatcctttt tttctgcgcg      960
taatctgctg cttgcaaaca aaaaaaccac cgctaccagc ggtggtttgt ttgccggatc     1020
aagagctacc aactcttttt ccgaaggtaa ctggcttcag cagagcgcag ataccaaata     1080
ctgtccttct agtgtagccg tagttaggcc accacttcaa gaactctgta gcaccgccta     1140
catacctcgc tctgctaatc ctgttaccag tggctgctgc cagtggcgat aagtcgtgtc     1200
ttaccgggtt ggactcaaga cgatagttac cggataaggc gcagcggtcg ggctgaacgg     1260
ggggttcgtg cacacagccc agcttggagc gaacgaccta caccgaactg agatacctac     1320
agcgtgagct atgagaaagc gccacgcttc ccgaagggag aaaggcggac aggtatccgg     1380
taagcggcag ggtcggaaca ggagagcgca cgagggagct tccaggggga aacgcctggt     1440
atctttatag tcctgtcggg tttcgccacc tctgacttga gcgtcgattt ttgtgatgct     1500
cgtcaggggg gcggagccta tggaaaaacg ccagcaacgc ggccttttta cggttcctgg     1560
ccttttgctg gccttttgct cacatgttct ttcctgcgtt atccctgat tctgtggata     1620 accgtattac cgcctttgag tgagctgata ccgctcgccg cagccgaacg accgagcgca     1680
gcgagtcagt gagcgaggaa gcggaagagc gcctgatgcg gtattttctc cttacgcatc     1740
tgtgcggtat ttcacaccgc aatggtgcac tctcagtaca atctgctctg atgccgcata     1800
gttaagccag tatacactcc gctatcgcta cgtgactggg tcatggctgc gccccgacac     1860
ccgccaacac ccgctgacgc gccctgacgg gcttgtctgc tcccggcatc cgcttacaga     1920
caagctgtga ccgtctccgg gagctgcatg tgtcagaggt tttcaccgtc atcaccgaaa     1980
cgcgcgaggc agctgcggta agctcatca gcgtggtcgt gaagcgattc acagatgtct     2040
gcctgttcat ccgcgtccag ctcgttgagt ttctccagaa gcgttaatgt ctggcttctg     2100
ataaagcggg ccatgttaag gcggttttt cctgtttgg tcactgatgc ctccgtgtaa     2160
gggggatttc tgttcatggg ggtaatgata ccgatgaaac gagagaggat gctcacgata     2220
cgggttactg atgatgaaca tgcccggtta ctggaacgtt gtgagggtaa acaactggcg     2280
gtatggatgc ggcgggacca gagaaaaatc actcagggtc aatgccagcg ctcatgagcc     2340
cgaagtggcg agcccgatct tccccatcgg tgatgtcggc gatataggcg ccagcaaccg     2400
cacctgtggc gccggtgatg ccggccacga tgcgtccggc gtagaggatc gagatccatt     2460
tacgttgaca ccatcgaatg gtgcaaaacc tttcgcggta tggcatgata gcgcccggaa     2520
gagagtcaat tcagggtggt gaatgtgaaa ccagtaacgt tatacgatgt cgcagagtat     2580
gccggtgtct cttatcagac cgtttcccgc gtggtgaacc aggccagcca cgtttctgcg     2640
aaaacgcggg aaaaagtgga agcggcgatg gcggagctga attacattcc caaccgcgtg     2700
```

```
gcacaacaac tggcgggcaa acagtcgttg ctgattggcg ttgccacctc cagtctggcc    2760
ctgcacgcgc cgtcgcaaat tgtcgcggcg attaaatctc gcgccgatca actgggtgcc    2820
agcgtggtgg tgtcgatggt agaacgaagc ggcgtcgaag cctgtaaagc ggcggtgcac    2880
aatcttctcg cgcaacgcgt cagtgggctg atcattaact atccgctgga tgaccaggat    2940
gccattgctg tggaagctgc ctgcactaat gttccggcgt tatttcttga tgtctctgac    3000
cagacaccca tcaacagtat tattttctcc catgaagacg gtacgcgact gggcgtggag    3060
catctggtcg cattgggtca ccagcaaatc gcgctgttag cgggcccatt aagttctgtc    3120
tcggcgcgtc tgcgtctggc tggctggcat aaatatctca ctcgcaatca aattcagccg    3180
atagcggaac gggaaggcga ctggagtgcc atgtccggtt ttcaacaaac catgcaaatg    3240
ctgaatgagg gcatcgttcc cactgcgatg ctggttgcca acgatcagat ggcgctgggc    3300
gcaatgcgcg ccattaccga gtccgggctg cgcgttggtg cggatatttc ggtagtggga    3360
tacgacgata ccgaagacag ctcatgttat atcccgccgt taaccaccat caaacaggat    3420
tttcgcctgc tggggcaaac cagcgtggac cgcttgctgc aactctctca gggccaggcg    3480
gtgaagggca atcagctgtt gcccgtctca ctggtgaaaa gaaaaaccac cctggcttga    3540
gaaatcataa aaaatttatt tgctttgtga gcggataaca attataatag attcaattgt    3600
gagcggataa caatttcaca catctagaaa taattttgtt taactttaag aaggagatat    3660
catatgaaga acattcaggg cattgtgttt gacctctatg gtacgctgta tgacgtacac    3720
agcgtcgttc aagcgtgtga agaagtttac cctggtcaag gcgatgcgat ttcccgtttg    3780
tggcgtcaga aacagctgga atacacgtgg ttgcgttcct tgatgggacg ctatgtcaac    3840
ttcgagaaag cgactgagga tgcgttacgc tttacctgta cgcacctggg tctgtcccct    3900
gacgacgaaa cccatcaacg tctgagcgat gcctatctcc acctgactcc gtacgcagat    3960
acagccgatg cagttcgtcg gttaaaagcc gcaggcttac cactgggggat catcagcaat    4020 ggcagtcatt gcagcattga acaggtggta accaactcgg aaatgaactg gctttcgat    4080 cagctgattt cggtcgaaga tgtccaggtg ttcaaacccg attctcgcgt gtattcactg    4140
gcggagaaac gcatgggctt tccgaaggag aacatcctct tcgtgagttc gaatgcttgg    4200
gatgcgtcag ctgcctctaa ctttgggttt ccggtttgct ggatcaatcg ccagaatggt    4260
gcgtttgacg aactggatgc caaaccgacc catgtggtac gcaatctggc agaaatgagc    4320
aattggcttg tgaacagtct ggactaactc gagcaccacc accaccacca ctgagatccg    4380
gctgctaaca aagcccgaaa ggaagctgag ttggctgctg ccaccgctga gcaataacta    4440
gcataacccc ttggggcctc taaacgggtc ttgaggggtt ttttgctgaa aggaggaact    4500
atatccggat aattc                                                    4515
```

<210> SEQ ID NO 8
<211> LENGTH: 4437
<212> TYPE: DNA
<213> ORGANISM: Artificial Sequence
<220> FEATURE:
<223> OTHER INFORMATION: pKA81a-HADH-vector with Haloacid Dehalogenase
      aus Sulfolobus tokodaii 7

<400> SEQUENCE: 8

```
ttagaaaaac tcatcgagca tcaaatgaaa ctgcaattta ttcatatcag gattatcaat      60
accatatttt tgaaaagcc gtttctgtaa tgaaggagaa aactcaccga ggcagttcca     120
taggatggca agatcctggt atcggtctgc gattccgact cgtccaacat caatacaacc     180
```

-continued

```
tattaatttc ccctcgtcaa aaataaggtt atcaagtgag aaatcaccat gagtgacgac      240
tgaatccggt gagaatggca aaagtttatg catttctttc cagacttgtt caacaggcca      300
gccattacgc tcgtcatcaa aatcactcgc atcaaccaaa ccgttattca ttcgtgattg      360
cgcctgagcg agacgaaata cgcgatcgct gttaaaagga caattacaaa caggaatcga      420
atgcaaccgg cgcaggaaca ctgccagcgc atcaacaata ttttcacctg aatcaggata      480
ttcttctaat acctggaatg ctgttttccc ggggatcgca gtggtgagta accatgcatc      540
atcaggagta cggataaaat gcttgatggt cggaagaggc ataaattccg tcagccagtt      600
tagtctgacc atctcatctg taacatcatt ggcaacgcta cctttgccat gtttcagaaa      660
caactctggc gcatcgggct tcccatacaa tcgatagatt gtcgcacctg attgcccgac      720
attatcgcga gccatttat acccatataa atcagcatcc atgttggaat taatcgcgg       780 cctagagcaa gacgtttccc gttgaatatg gctcataaca ccccttgtat tactgtttat      840
gtaagcagac agttttattg ttcatgacca aaatccctta acgtgagttt cgttccact       900 gagcgtcaga ccccgtagaa aagatcaaag gatcttcttg atccttttt tttctgcgcg       960 taatctgctg cttgcaaaca aaaaaaccac cgctaccagc ggtggtttgt ttgccggatc     1020
aagagctacc aactctttt ccgaaggtaa ctggcttcag cagagcgcag ataccaaata     1080
ctgtccttct agtgtagccg tagttaggcc accacttcaa gaactctgta gcaccgccta    1140
catacctcgc tctgctaatc ctgttaccag tggctgctgc cagtggcgat aagtcgtgtc    1200
ttaccgggtt ggactcaaga cgatagttac cggataaggc gcagcggtcg ggctgaacgg    1260
ggggttcgtg cacacagccc agcttggagc gaacgaccta caccgaactg agatacctac    1320
agcgtgagct atgagaaagc gccacgcttc ccgaagggag aaaggcggac aggtatccgg    1380
taagcggcag ggtcggaaca ggagagcgca cgagggagct tccaggggga aacgcctggt    1440
atctttatag tcctgtcggg tttcgccacc tctgacttga gcgtcgattt ttgtgatgct    1500
cgtcaggggg gcggagccta tggaaaaacg ccagcaacgc ggccttttta cggttcctgg    1560
ccttttgctg gccttttgct cacatgttct ttcctgcgtt atccctgat tctgtggata     1620 accgtattac cgcctttgag tgagctgata ccgctcgccg cagccgaacg accgagcgca    1680
gcgagtcagt gagcgaggaa gcggaagagc gcctgatgcg gtattttctc cttacgcatc    1740
tgtgcggtat ttcacaccgc aatggtgcac tctcagtaca atctgctctg atgccgcata    1800
gttaagccag tatacactcc gctatcgcta cgtgactggg tcatggctgc gccccgacac    1860
ccgccaacac ccgctgacgc gccctgacgg gcttgtctgc tcccggcatc cgcttacaga    1920
caagctgtga ccgtctccgg gagctgcatg tgtcagaggt tttcaccgtc atcaccgaaa    1980
cgcgcgaggc agctgcggta agctcatca gcgtggtcgt gaagcgattc acagatgtct    2040
gcctgttcat ccgcgtccag ctcgttgagt ttctccagaa gcgttaatgt ctggcttctg    2100
ataaagcggg ccatgttaag gcggtttttt cctgtttgg tcactgatgc ctccgtgtaa     2160
gggggatttc tgttcatggg gtaatgata ccgatgaaac gagagaggat gctcacgata     2220
cgggttactg atgatgaaca tgcccggtta ctggaacgtt gtgagggtaa caactggcg     2280 gtatggatgc ggcgggacca gagaaaaatc actcagggtc aatgccagcg ctcatgagcc    2340
```

```
cgaagtggcg agcccgatct tccccatcgg tgatgtcggc gatataggcg ccagcaaccg    2400
cacctgtggc gccggtgatg ccggccacga tgcgtccggc gtagaggatc gagatccatt    2460
tacgttgaca ccatcgaatg gtgcaaaacc tttcgcggta tggcatgata gcgcccggaa    2520
gagagtcaat tcagggtggt gaatgtgaaa ccagtaacgt tatacgatgt cgcagagtat    2580
gccggtgtct cttatcagac cgtttcccgc gtggtgaacc aggccagcca cgtttctgcg    2640
aaaacgcggg aaaagtggaa gcggcgatg cggagctga attacattcc caaccgcgtg    2700
gcacaacaac tggcgggcaa acagtcgttg ctgattggcg ttgccacctc cagtctggcc    2760
ctgcacgcgc cgtcgcaaat tgtcgcggcg attaaatctc gcgccgatca actgggtgcc    2820
agcgtggtgg tgtcgatggt agaacgaagc ggcgtcgaag cctgtaaagc ggcggtgcac    2880
aatcttctcg cgcaacgcgt cagtgggctg atcattaact atccgctgga tgaccaggat    2940
gccattgctg tggaagctgc ctgcactaat gttccggcgt tatttcttga tgtctctgac    3000
cagacaccca tcaacagtat tattttctcc catgaagacg gtacgcgact gggcgtggag    3060
catctggtcg cattgggtca ccagcaaatc gcgctgttag cgggcccatt aagttctgtc    3120
tcggcgcgtc tgcgtctggc tggctggcat aaatatctca ctcgcaatca aattcagccg    3180
atagcggaac gggaaggcga ctggagtgcc atgtccggtt ttcaacaaac catgcaaatg    3240
ctgaatgagg gcatcgttcc cactgcgatg ctggttgcca acgatcagat ggcgctgggc    3300
gcaatgcgcg ccattaccga gtccgggctg cgcgttggtg cggatatttc ggtagtggga    3360
tacgacgata ccgaagacag ctcatgttat atcccgccgt taaccaccat caaacaggat    3420
tttcgcctgc tggggcaaac cagcgtggac cgcttgctgc aactctctca gggccaggcg    3480
gtgaagggca atcagctgtt gcccgtctca ctggtgaaaa gaaaaccac cctggcttga    3540 gaaatcataa aaaatttatt tgctttgtga gcggataaca attataatag attcaattgt    3600
gagcggataa caatttcaca catctagaaa taattttgtt taactttaag aaggagatat    3660
catatgatca ttctggcctt tgatatcttt ggtactgtac tcgatacatc taccgttatc    3720
caggaatttc gcaacaaaca actggagtat acttggctgc tgacgattat gggcaaatac    3780
gtggaatttg aggaaatcac caaaattacg ttacgctata tcctgaaagt tcgtggtgaa    3840
gaatcgaagt ttgacgaaga actgaacaaa tggaagaacc tgaaagcgta tgaagatacc    3900 aaataccttaa aagagatttc ggaaattgcc gaagttatg cgctgtcaaa tgggagtatt    3960
aacgaagtga acagcatttt ggaacgtaat gggttacttc ggtacttcaa aggcatttc    4020 tccgcagaaa gcgttaaaga gtacaaaccg agtccgaaag tgtataagta ctttctggat    4080
agcattggtg cgaaagaagc cttcttggta tctagcaacg cattcgatgt gattggcgct    4140
aagaatgctg gtatgcgttc catctttgtc aatcgcaaga acaccattgt cgatcctatc    4200
ggcggaaaac cagacgtgat cgtcaatgac ttcaaagagc tgtatgagtg gattctccgc    4260
tataaataac tcgagcacca ccaccaccac cactgagatc cggctgctaa caaagcccga    4320
aaggaagctg agttggctgc tgccaccgct gagcaataac tagcataacc ccttggggcc    4380
tctaaacggg tcttgagggg ttttttgctg aaaggaggaa ctatatccgg ataattc       4437
```

METHOD FOR THE PREPARATION OF CHIRAL ALPHA HALOALKANOIC ACIDS

CROSS-REFERENCE TO RELATED APPLICATIONS

This application is the National Stage entry of International Application No. PCT/EP2018/075752, filed 24 Sep. 2018, which claims priority to European Patent Application No. 17193736.0, filed 28 Sep. 2017.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2923343-637000_ST25.txt" created on 24 Mar. 2020, and 19,952 bytes in size) is submitted concurrently with the instant application, and the entire contents of the Sequence Listing are incorporated herein by reference.

BACKGROUND

Description of Related Art

It is well known that there is sometimes a marked difference in the effects of enantiomers of the same chemical substance in biological systems such as organisms. In drugs, for example, often only one of a drug's enantiomers is responsible for the desired physiologic effects, while the other enantiomer is less active, inactive, or sometimes counteractive.

Therefore, different methods for obtaining only the desired enantiomer exist. One strategy is known as chiral resolution. This method involves preparing the compound in racemic form, and separating it into the different enantiomers. Another strategy is asymmetric synthesis i.e. the use of various techniques to prepare the desired compound in high enantiomeric excess.

A class of molecules existing as racemic mixture are alpha haloalkanoic acids. The R or the S enantiomer of these alpha haloalkanoic acids can for analytical purposes be separated for example via capillary gas chromatography as described in U.S. Pat. No. 5,154,738. For synthetic purposes the most practical way to prepare chiral alpha haloalkanoic acids is via racemic resolution using strychnine or brucine salts or by stereoselective bromination of R-2-aminobutyric acids. However, the chiral precursors or reagents for these reactions—e.g. [R-2-aminobutyric acid]—are not cost effective. In addition, the reactions are difficult to pursue on a larger or even industrial scale. The stereoselective bromination of R-2-aminobutyric acid for example is time consuming, requires low temperatures (−10 to 5° C.) and reaction progression is hard to monitor. Moreover, nitroseous gases are formed during the reaction which represents an occupational safety issue.

SUMMARY

Thus, it was the object of the current invention to devise an alternative, more cost effective, time-efficient and safer method to enable and/or facilitate the separation of the R and S enantiomers of alpha haloalkanoic acids of Formula I.

The invention achieves this object by provision of a method of selectively hydrolyzing the S-enantiomer of an alpha haloalkanoic acid according to Formula I,

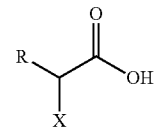

wherein X is a halogen and
R is an alkyl chain of 1 to 6 carbon atoms, wherein that said alkyl chain can be straight or branched at carbon atoms γ or δ,
comprising
   providing a racemate of the R-enantiomer and the S-enantiomer of said alpha haloalkanoic acid,
   providing a polypeptide having dehalogenase activity comprising an amino acid sequence as set forth in SEQ ID NO. 1 or SEQ ID NO. 4 or a sequence with at least 80% sequence identity to either of said sequences,
   reacting the racemate for 1-8 hours, wherein
   the pH is in the range of 9-10 and the temperature is in the range of 15-35° C. for the polypeptide with dehalogenase activity comprising an amino acid sequence as set forth in SEQ ID NO. 1 or a sequence with at least 80% sequence identity to said sequence or
   the pH is in the range of 9-10 and the temperature is in the range of 55-65° C. for the polypeptide with dehalogenase activity comprising an amino acid sequence as set forth in SEQ ID NO. 4 or a sequence with at least 80% sequence identity to said sequence.
   and wherein an enantiomeric excess of the R-enantiomer of between 90.0 and 99.9% is reached after 1-8 hours.

BRIEF DESCRIPTION OF THE DRAWINGS

FIGS. 1-5 depict embodiments as described herein.

DETAILED DESCRIPTION OF A PREFERRED EMBODIMENT

Figure 1:
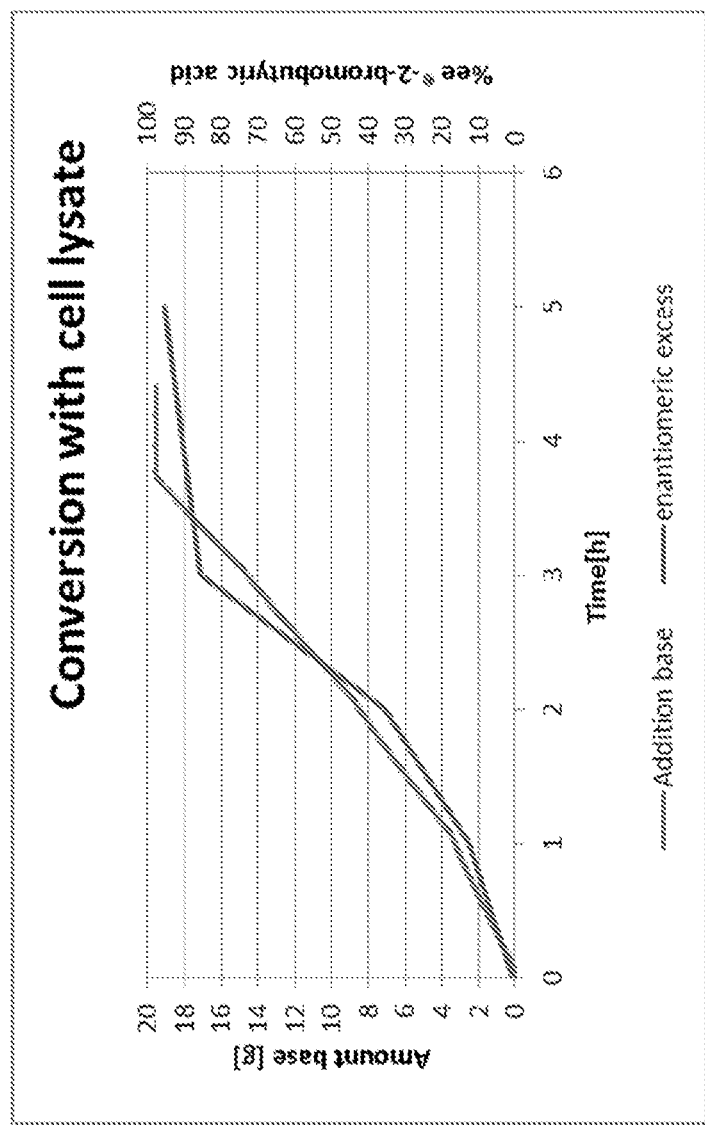

This method has the advantage that it is an alternative, more cost effective and time-efficient method based on differing reaction behavior of the R and S enantiomers of alpha haloalkanoic acids of Formula I enabling and/or facilitating the separation of the two enantiomers, since the polypeptide with dehalogenase activity comprising an amino acid sequence as set forth in SEQ ID NO.1 or SEQ ID NO 4 or a sequence with at least 80% sequence identity to either of said sequences selectively hydrolyses the S enantiomer of alpha haloalkanoic acids of Formula I very efficiently under the given reaction conditions, i.e. achieves a high space-time yield. The selectivity of the hydrolysis reaction is shown by an enantiomeric excess rate of the remaining R-enantiomer of between 90 and 99%. In other words, it was surprisingly found that the specified conditions facilitate a more cost effective, time-efficient and safer method to derive the R-enantiomer.

As stated above the polypeptide with dehalogenase activity comprising an amino acid sequence as set forth in SEQ ID NO.1 or SEQ ID NO 4 or a sequence with at least 80% sequence identity to either of said sequences selectively hydrolyses the S enantiomer of alpha haloalkanoic acids of Formula I very efficiently under the given reaction conditions. During this reaction the R-enantiomer remains unchanged, while the S-enantiomer is hydrolyzed under conversion of its stereoisomerism.

In preferred embodiments of said method the polypeptide having dehalogenase activity comprises the amino acid sequence as set forth in SEQ ID NO 4 or a sequence with at least 80% sequence identity to said sequence and X is fluor in the alpha haloalkanoic acid according to Formula I. It was surprisingly found for the first time that under these conditions and using the polypeptide having dehalogenase activity comprising the amino acid sequence as set forth in SEQ ID NO 4 or a sequence with at least 80% sequence identity to said sequence also the S-enantiomer of a fluor containing alpha haloalkanoic acid according to formula I was selectively hydrolyzed, wherein an enantiomeric excess of the R-enantiomer of between 90.0 and 99.9% was reached after 1-8 hours.

The term "comprising" is to be interpreted as specifying the presence of the stated parts, steps or components, but does not exclude the presence of one or more additional parts, steps or components.

It is understood that when referring to a word in the singular, the plural is also included herein. Thus, reference to an element by the indefinite article "a" or "an" does not exclude the possibility that more than one of the element is present, unless the context clearly requires that there be one and only one of the elements. The indefinite article "a" or "an" thus usually means "at least one".

As used herein the term "enantiomer" refers to one of two stereoisomers of a given molecule that are mirror images of each other that are non-superimposable (not identical). A single chiral atom or similar structural feature in a compound causes that compound to have two possible structures which are non-superimposable, each a mirror image of the other.

As used herein the term "racemate" or "racemic substrate" refers to a mixture that has equal amounts of the two stereoisomers of a chiral molecule.

As mentioned above, in the case of the polypeptide with dehalogenase activity comprising an amino acid sequence as set forth in SEQ ID NO. 1 or a sequence with at least 80% sequence identity to SEQ ID NO. 1 X of Formula I is selected from a halogen other than fluor and the method described above is carried out for 1-8 hours, wherein the pH is in the range of 9-10 and the temperature is in the range of 15-35° C.

Using these conditions is was surprisingly found that the polypeptide with dehalogenase activity comprising an amino acid sequence as set forth in SEQ ID NO. 1 or a sequence with at least 80% sequence reliably reached enantiomeric excess rate values of above 99% (cf. FIG. 3) and a space time yield of 16.6 $g_{product}$ $L^{-1}$ $h^{-1}$ (at a substrate concentration of 100 g/l)

It should be noted, that due to the racemic substrate the maximum yield of the R-enantiomer is 50%, thus the maximum yield using a substrate concentration of 100 g/l would be 50 g/l. Moreover, the space time yield would be even higher, if lower substrate concentrations—e.g. 50 g/l— are employed. However, higher substrate concentrations are beneficial to a production process on industrial scale.

In preferred embodiments the method described above in the case of the polypeptide with dehalogenase activity comprising an amino acid sequence as set forth in SEQ ID NO. 1 or a sequence with at least 80% sequence identity to it, is carried out for 4-6 hours, wherein the pH is 9.5 and the temperature is in the range of 20-30° C. Using these conditions a full conversion i.e. 90% ee can be reached after 3 h.

In an especially preferred embodiment of this reaction the temperature is 25° C.

The pH is preferably in the range of 9-10 and most preferably at 9.5.

A reaction temperature of 25° C. and a pH of 9.5 reached a full conversion i.e. 90% ee after 1 h. Thus these conditions lead to an especially high space time yield. In the case of the polypeptide with dehalogenase activity comprising an amino acid sequence as set forth in SEQ ID NO. 1 or a sequence with at least 80% sequence identity to it, provided as freshly fermented biomass (i.e. the polypeptide is contained in whole cells) the achieved space time yield was 50 $g_{product}$ $L^{-1}$ $h^{-1}$ As mentioned above, in the case of the polypeptide with dehalogenase activity comprising an amino acid sequence as set forth in SEQ ID NO. 4 or a sequence with at least 80% sequence identity to the method described above is carried out for 1-8 hours, wherein the pH is in the range of 9-10 and the temperature is in the range of 55-65° C. and an enantiomeric excess of the R-enantiomer of between 90.0 and 99.9% is reached after 1-8 hours. In a preferred embodiment the method described above in the case of the polypeptide with dehalogenase activity comprising an amino acid sequence as set forth in SEQ ID NO. 4 or a sequence with at least 80% sequence identity to it, is carried out for 4-6 hours, wherein the pH is 9.5 and the temperature is in the range of 59–61° C.

In an especially preferred embodiment of this reaction the temperature is 60° C.

The pH is preferably in the range of 9-10 and most preferably at 9.5.

In a preferred embodiment of the polypeptide with dehalogenase activity described herein, said polypeptide has at least 80% sequence identity, more preferably at least 85% sequence identity, more preferably at least 90% sequence identity, more preferably at least 95% sequence identity, more preferably at least 95%, 96%, 97%, 98%, 99%, and most preferably 100% sequence identity to SEQ ID NO 1 or said polypeptide has at least 80% sequence identity, more preferably at least 85% sequence identity, more preferably at least 90% sequence identity, more preferably at least 95% sequence identity, more preferably at least 95%, 96%, 97%, 98%, 99%, and most preferably 100% sequence identity to SEQ ID NO 4.

The polypeptides with dehalogenase activity comprising an amino acid sequence as set forth in SEQ ID NO 1 or SEQ ID NO 4 can also be characterized via their nucleic acid sequences.

Thus, in case of the polypeptide with dehalogenase activity comprising an amino acid sequence as set forth in SEQ ID NO. 1 the provided polypeptide is selected from the group a) a polypeptide comprising an amino acid sequence as set forth in SEQ ID NO. 1 or a sequence with at least 80% sequence identity to said sequence, b) an isolated codon optimized nucleic acid fragment comprising a nucleotide sequence of at least 80% sequence identity to SEQ ID NO. 2 c) an isolated nucleic acid fragment comprising a sequence complementary to SEQ ID NO. 2, d) an isolated nucleic acid fragment comprising a sequence which specifically hybridizes to said isolated nucleic acid fragment of b) or said complementary of c)

e) an isolated nucleic acid fragment comprising a nucleotide sequence of at least 80% sequence identity to SEQ ID NO. 3 f) an isolated nucleic acid fragment comprising a sequence complementary to SEQ ID NO. 3, g) an isolated nucleic acid fragment comprising a sequence which specifically hybridizes to said isolated nucleic acid fragment of e) or said complementary of f).

Thus, in the case of the polypeptide with dehalogenase activity comprising an amino acid sequence as set forth in SEQ ID NO. 1 the polypeptide can be encoded by different nucleic acids sequences. This is a result of the degeneracy of the genetic code.

As a result of this degeneracy of the genetic code, amino acids can be encoded by one or more codons. In different organisms, the codons coding for an amino acid are used at different frequencies. Adapting the codons of a coding nucleic acid sequence to the frequency of their use in the organism in which the sequence to be expressed is to be integrated may contribute to an increased amount of translated protein and/or to the stability of the mRNA in question in the particular cells The frequency of use of codons in the host cells or hosts in question can be determined by the person skilled in the art by examining as many coding nucleic acid sequences of the organism in question as possible in terms of the frequency with which certain codons are used for coding a certain amino acid. The frequency of the use of codons of certain organisms is known to the person skilled in the art (cf. www(dot)kazusa(dot)or(dot)jp/codon/) and can be determined in a simple and rapid manner using specifically developed algorithms implemented into computer programs (e.g. Grote et al., 2005, Nucleic Acids Research 33, W526W531; doi: 10.1093/nar/gki376). Tools using such algorithms are publicly accessible and are provided for free as web-interfaces inter alia on the World Wide Web from various institutions, like the European Bioinformatics Institute (EMBL-EBI) and others (for example www(dot)jcat(dot)de; gcua(dot)schoedl(dot)de/; www(dot)kazusa(dot)or(dot)jp/codon/; www(dot)entelechon(dot)com/eng/cutanalysis(dot)html; www(dot)ebi(dot)ac(dot)uk/Tools/st/emboss backtranseq/). Adapting the codons of a coding nucleic acid sequence to the frequency of their use in an organism in which the sequence is intended to be expressed can be carried out by in vitro mutagenesis or, preferably, by de novo synthesis of the gene sequence. Methods for the de novo synthesis of nucleic acid sequences are known to the person skilled in the art. A de novo synthesis can be carried out, for example, by initially synthesizing individual nucleic acid oligonucleotides, hybridizing these with oligonucleotides complementary thereto, so that they form a DNA double strand, and then ligating the individual double-stranded oligonucleotides such that the desired nucleic acid sequence is obtained. The de novo synthesis of nucleic acid sequences including the adaptation of the frequency with which the codons are used to a certain target organism can also be sourced out to companies offering this service (for example Eurofins MWG).

The isolated nucleic acid fragments comprising a nucleotide sequence of at least 80% sequence identity to SEQ ID NO. 2 or SEQ ID NO 3 preferably have at least 85% sequence identity, more preferably at least 90% sequence identity, more preferably at least 95% sequence identity, more preferably at least 95%, 96%, 97%, 98%, 99%, and most preferably 100% sequence identity to SEQ ID NO. 2 or SEQ ID NO 3, respectively.

In the case of the polypeptide with dehalogenase activity comprising an amino acid sequence as set forth in SEQ ID NO. 4 the provided polypeptide is selected from the group a) a polypeptide comprising an amino acid sequence as set forth in SEQ ID NO. 4 or a sequence with at least 80% sequence identity to said sequence, b) an isolated codon optimized nucleic acid fragment comprising a nucleotide sequence of at least 80% sequence identity to SEQ ID NO. 5 c) an isolated nucleic acid fragment comprising a sequence complementary to SEQ ID NO. 5, d) an isolated nucleic acid fragment comprising a sequence which specifically hybridizes to said isolated nucleic acid fragment of b) or said complementary of c)

e) an isolated nucleic acid fragment comprising a nucleotide sequence of at least 80% sequence identity to SEQ ID NO. 6 f) an isolated nucleic acid fragment comprising a sequence complementary to SEQ ID NO. 6, g) an isolated nucleic acid fragment comprising a sequence which specifically hybridizes to said isolated nucleic acid fragment of e) or said complementary of f).

Also the polypeptide with dehalogenase activity—here the polypeptide comprising an amino acid sequence as set forth in SEQ ID NO. 4—can be encoded for by different nucleic acids sequences. Again this is a result of the degeneracy of the genetic code as explained above.

Again, the isolated nucleic acid fragments comprising a nucleotide sequence of at least 80% sequence identity to SEQ ID NO. 5 or SEQ ID NO 6 preferably have at least 85% sequence identity, more preferably at least 90% sequence identity, more preferably at least 95% sequence identity, more preferably at least 95%, 96%, 97%, 98%, 99%, and most preferably 100% sequence identity to SEQ ID NO. 5 or SEQ ID NO 6, respectively.

As used herein the term "hydrolysis" is the enzymatically catalyzed hydrolytic cleavage of a carbon-halogen bond, in which the halogen is replaced by a hydroxyl group. Some enzymes catalyze the hydrolytic dehalogenation of 2-haloalkanoic acids to produce the corresponding 2-hydroxyalkanoic acids.

As used herein the term "selectively hydrolyzing" refers to the fact that some enzymes (i.e. polypeptides) that catalyze a hydrolysis show stereoselective activity. In other words, via selective hydrolysis an enantiomeric excess of either the R- or the S-enantiomer is generated depending on the preference of the enzyme.

As used herein the term "enantiomeric excess" or "ee-value" refers to a measurement for the purity of chiral substances. It reflects the degree to which a sample contains one enantiomer in greater amounts than the other. A racemic mixture has an ee of 0%, while a single completely pure enantiomer has an ee of 100%. A sample with 70% of one enantiomer and 30% of the other has an ee of 40% (70%-30%).

Methods for determining the ee-value are known in the art. It can e.g. be determined using gas chromatography devices, equipped with a chiral column.

Thus, the polypeptides described herein show stereoselective activity when catalyzing a hydrolysis reaction. This stereoselective activity can be expressed as ee value. As stated above the polypeptides having dehalogenase activity comprising an amino acid sequence as set forth in SEQ ID NO. 1 or SEQ ID NO. 4 or a sequence with at least 80% sequence identity to either of said sequences show stereoselective activity reaching very high ee values.

A reliably assertion of the suitability of a given enzyme for a given reaction can be made using the parameters: substrate conversion, product formation, enantiomeric excess (ee) and space time yield (STY). As used herein the term "space time yield" refers to the amount of product generated from a given substrate concentration in a specific volume in a defined time.

In some instances space time yield values given herein are also set in relation to the specific amount of cell extract or of whole cells used in the given reaction (cf. Examples 3 and 5).

As used herein the term "gene" means a DNA sequence made up of nucleotides comprising a region (transcribed region), which is transcribed into an RNA molecule (e.g. directly into a mRNA without intron sequences) in a cell, operably linked to regulatory regions capable of regulating the expression of the polypeptide. A gene may thus comprise several operably linked sequences, such as untranslated regulatory regions (e.g. a promoter, enhancer, repressor), a 5' leader sequence comprising e.g. sequences involved in translation initiation, a (protein) coding region (cDNA or genomic DNA) and a 3' non-translated sequence comprising e.g. transcription termination sites.

As used herein the term "expression of a gene" or "gene expression" refers to the process wherein a DNA region (the coding region), which is operably linked to appropriate regulatory regions, particularly a promoter, is transcribed into an mRNA molecule. The mRNA molecule is then processed further (by post-transcriptional processes) within the cell, e.g. by translation initiation and translation into an amino acid chain (polypeptide), and translation termination by translation stop codons.

As used herein the term "Wild type" (also written "wild-type" or "wild-type"), refers to a typical form of an enzyme or a gene as it most commonly occurs in nature.

As used herein the term "polypeptide" refers to any peptide, polypeptide, oligopeptide or protein. A polypeptide consists of consecutive amino acids, which are linked by peptide bonds. The polymer may be linear or branched, it may comprise modified amino acids, and it may be interrupted by non-amino acids. The polypeptide may be human, non-human, and an artificial or chemical mimetic of a corresponding naturally occurring amino acid, as well as to naturally occurring amino acid polymers and non-naturally occurring amino acid polymer. The term also encompasses an amino acid polymer that has been modified by either natural processes or by chemical modifications; for example, by disulfide bond formation, glycosylation, lipidation, acetylation, acylation, phosphorylation, or any other manipulation, such as conjugation with a labeling component, such as but not limited to, fluorescent markers, particles, biotin, beads, proteins, radioactive labels, chemiluminescent tags, bioluminescent labels, and the like.

As used herein the term "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length. In other words if two identical sequences are aligned the sequence identity value would be 100%.

Aligned sequences of nucleotide or amino acid residues are typically represented as rows within a matrix. Gaps are inserted between the residues so that identical or similar characters are aligned in successive columns.

In order to determine the sequence identity the Needleman and Wunsch global alignment algorithm (Needleman and Wunsch, 1970, J Mol Biol 48(3):443-53) of The European Molecular Biology Open Software Suite (EMBOSS, Rice et al., 2000, Trends in Genetics 16(6): 276277; see e.g. www(dot)ebi(dot)ac(dot)uk/emboss/align/index(dot)html) using default settings (gap opening penalty=10 (for nucleotides)/10 (for proteins) and gap extension penalty=0.5 (for nucleotides)/0.5 (for proteins)) can be employed. For nucleotides the default scoring matrix used is EDNAFULL and for proteins the default scoring matrix is EBLOSUM62.

The term "nucleic acid molecule" is intended to indicate any single- or double stranded nucleic acid molecule comprising DNA (cDNA and/or genomic DNA), RNA (preferably mRNA), PNA, LNA and/or Morpholino.

The term "vector", as used herein, refers to a molecular vehicle used to transfer foreign genetic material into another cell. The vector itself is generally a DNA sequence that consists of an insert (sequence of interest) and a larger sequence that serves as the "backbone" of the vector. The purpose of a vector to transfer genetic information to another cell is typically to isolate, multiply, or express the insert in the target cell.

The term "plasmid", as used herein, refers to plasmid vectors, i.e. circular DNA sequence that are capable of autonomous replication within a suitable host due to an origin of replication ("ORI"). Furthermore, a plasmid may comprise a selectable marker to indicate the success of the transformation or other procedures meant to introduce foreign DNA into a cell and a multiple cloning site which includes multiple restriction enzyme consensus sites to enable the insertion of an insert. Plasmid vectors called cloning or donor vectors are used to ease the cloning and to amplify a sequence of interest. Plasmid vectors called expression or acceptor vectors are specifically for the expression of a gene of interest in a defined target cell. Those plasmid vectors generally show an expression cassette, consisting of a promoter, a ribosomal binding site, the transgene and a terminator sequence. For expression control those plasmids contains a repressor, which is localized on the plasmid backbone. Expression plasmids can be shuttle plasmids containing elements that enable the propagation and selection in different host cells.

As used herein the term "specifically hybridize" or "selectively hybridize" refers to a reaction of the nucleic acid sequence in question in a hybridization solution containing 0.5 M sodium phosphate buffer, pH 7.2 containing 7% SDS, 1 mM EDTA and 100 mg/ml of salmon sperm DNA at 65° C. for 16 hours and washing twice at 65° C. for twenty minutes in a washing solution containing 9.5×SSC and 0.1% SDS.

In one embodiment of the method described herein the polypeptide with dehalogenase activity comprising an amino acid sequence as set forth in SEQ ID NO. 1 or SEQ ID NO. 4 or a sequence with at least 80% sequence identity to either of said sequences is provided as cell lysate and/or is comprised within whole cells.

As used herein the term "whole cells" refers to the fact that the polypeptide with dehalogenase activity comprising an amino acid sequence as set forth in SEQ ID NO. 1 or SEQ ID NO. 4 or a sequence with at least 80% sequence identity to either of said sequences is provided in the cells it is expressed in i.e. that the cell walls of said cells were not purposefully disrupted.

Said whole cells can be for example fresh biomass generated in a fermentation process. Alternatively, the whole cells can be frozen prior to use.

In other words, it was surprisingly found that even though the enzyme i.e. the polypeptide with dehalogenase activity comprising an amino acid sequence as set forth in SEQ ID NO. 1 or SEQ ID NO. 4 or a sequence with at least 80% sequence identity to either of said sequences, which is expressed by the (recombinant) whole cells, is only present within the cell the bioavailability of the substrate is sufficient that the enzyme can react with the substrate within the cell.

It was found that the *E. coli* cells used for enzyme synthesis produced the desired enzyme at a constant proportion of the total protein content. In other words, a given amount of total cellular protein (e.g. 5 g) always comprises the same amount of soluble enzyme concentration. Also for this reason, whole cells could be used in the experiments instead of cell lysate.

The use of whole cells has the advantage that not expensive and time consuming methods for provision of a cell extract have to be employed.

In one embodiment, said whole cells are *E. coli* cells selected from the group MG1655, W3110, JM101, BL21DE3, DH5alpha.

Moreover, the chosen *E. coli* preferably harbor the plasmid of SEQ ID NO. 7 and express the enzyme consisting of SEQ ID NO. 1 from the plasmid.

Alternatively, the chosen *E. coli* harbor the plasmid of SEQ ID NO. 8 and express the enzyme consisting of SEQ ID NO. 4 from the plasmid.

In one embodiment of the method described herein the polypeptide with dehalogenase activity comprising an amino acid sequence as set forth in SEQ ID NO. 1 or SEQ ID NO. 4 or a sequence with at least 80% sequence identity to either of said sequences is added at the start of the reaction to the racemate of said alpha haloalkanoic acid according to Formula I or said polypeptide with dehalogenase activity is added at the start and at different time points during the reaction to the racemate of said alpha haloalkanoic acid.

Surprisingly, the different dosage profiles have no influence on process performance. Thus, a person skilled in the art can choose the dosing profile most suitable for the process in question. This property of the claimed enzymes offers maximal flexibility for employing the enzyme in a given production process.

In one embodiment of the method described herein the polypeptide with dehalogenase activity polypeptide having dehalogenase activity comprising an amino acid sequence as set forth in SEQ ID NO. 1 or SEQ ID NO. 4 or a sequence with at least 80% sequence identity to either of said sequences is added at the start and at different time points during the reaction to the racemate of said alpha haloalkanoic acid, wherein the added polypeptide concentration is the same at each time point.

In one embodiment of the method described herein the polypeptide with dehalogenase activity comprising an amino acid sequence as set forth in SEQ ID NO. 1 or SEQ ID NO. 4 or a sequence with at least 80% sequence identity to either of said sequences is added at the start and at different time points during the reaction to the racemate of said alpha haloalkanoic acid, wherein the added polypeptide concentration differs at different time points.

In one embodiment of the method described herein the racemate is added to the polypeptide with dehalogenase activity polypeptide having dehalogenase activity comprising an amino acid sequence as set forth in SEQ ID NO. 1 or SEQ ID NO. 4 or a sequence with at least 80% sequence identity to either of said sequences or said polypeptide with dehalogenase activity is added to the racemate.

In case the racemate of said alpha haloalkanoic acid according to Formula I is added to the polypeptide with dehalogenase activity comprising an amino acid sequence as set forth in SEQ ID NO. 1 or SEQ ID NO. 4 or a sequence with at least 80% sequence identity to either of said sequences, preferably all of the racemate of said alpha haloalkanoic acid according to Formula I is added at the start of the reaction, wherein the pH value of the racemate is optimized for the reaction conditions prior to the addition.

Surprisingly, it has no influence on process performance whether the racemate of said alpha haloalkanoic acid according to Formula I, i.e. the substrate is added to the polypeptide with dehalogenase activity comprising an amino acid sequence as set forth in SEQ ID NO. 1 or SEQ ID NO. 4 or a sequence with at least 80% sequence identity to either of said sequences or whether said polypeptide with dehalogenase activity is added to the racemate of said alpha haloalkanoic acid according to Formula I.

In one embodiment of the method described herein either of the two polypeptides with dehalogenase activity as described herein is provided as whole cells at a pH of 9.5 and the racemate of said alpha haloalkanoic acid according to Formula I is added to the polypeptide, wherein the racemate of said alpha haloalkanoic acid according to Formula I is also provided at a pH of 9.5 and the pH of 9.5 is kept constant during the reaction via titration with a suitable base.

The suitable base can for example be chosen from the group consisting of aqueous KOH or NaOH.

In some embodiments of the method described herein the concentration of the racemate of said alpha haloalkanoic acid according to Formula I is between 80 and 200 g/L, preferably between 90 and 150 g/L most preferably it is 100 g/L. In other words, the concentration of the racemate of the alpha haloalkanoic acid is preferably chosen in such a manner that a full conversion can be reached.

In one embodiment of the method described herein the polypeptide with dehalogenase activity comprising an amino acid sequence as set forth in SEQ ID NO. 1 or SEQ ID NO. 4 or a sequence with at least 80% sequence identity to either of said sequences is provided as active whole cells and the biomass of said active whole cells has a concentration of between 15-200 g/L, preferably of between 25-100 g/L.

In some embodiments of the method described herein the ratio of racemate of the alpha haloalkanoic acid according to Formula I to biomass of whole cells comprising the polypeptide having dehalogenase activity comprising an amino acid sequence as set forth in SEQ ID NO. 1 or SEQ ID NO. 4 or a sequence with at least 80% sequence identity to either of said sequences is between 2:1 to 15:1, preferably between 3:1 to 10:1 most preferably 4:1.

As the polypeptide having dehalogenase activity comprising an amino acid sequence as set forth in SEQ ID NO. 1 or SEQ ID NO. 4 or a sequence with at least 80% sequence identity to either of said sequences is inhibited by higher substrate concentration, the ratio of substrate—i.e. alpha haloalkanoic acid according to Formula I—to enzyme—i.e. polypeptide having dehalogenase activity comprising an amino acid sequence as set forth in SEQ ID NO. 1 or SEQ ID NO. 4 or a sequence with at least 80% sequence identity to either of said sequences is comprised in whole cells and hence provided as biomass—increases with lower substrate concentrations.

In one embodiment of the method described herein the halogen X of said alpha haloalkanoic acid according to Formula I is chosen from the group consisting of bromide and chloride.

In one embodiment of the method described herein the moiety R of said alpha haloalkanoic acid according to Formula I is an alkyl chain of 1 to 6 carbon atoms, wherein that said alkyl chain is carbon atoms gamma or delta, and wherein the carbon atoms following the branch at carbon atoms γ or δ are cyclic.

In one embodiment of the method described herein the moiety R of said alpha haloalkanoic acid according to Formula I is chosen from the group consisting of ethyl, butyl, 2-methyl-propyl and methyl-cyclopropyl.

In one embodiment of the method described herein the pH value is kept constant via titration with a suitable base such as potassium hydroxide or sodium hydroxide.

Since it was found that the reaction conditions can be easily scaled up reaction volumes between 1 ml and several 1000 liters are possible.

In one embodiment of the method described herein said polypeptide with dehalogenase activity comprising an amino acid sequence as set forth in SEQ ID NO. 1 or SEQ ID NO. 4 or a sequence with at least 80% sequence identity to either of said sequences is a haloacid dehalogenase.

In a preferred embodiment of the method described herein the polypeptide with dehalogenase activity consists of the sequence of SEQ ID NO 1 and reacts with a racemic substrate selected from the group consisting of 2-chloro butyric acid, 2-bromo-hexanoic acid, 2-bromo-4-methyl pentanoic acid and 2-bromo-3-cyclopropyl-propanoic acid.

In an alternative preferred embodiment the of the method described herein the polypeptide with dehalogenase activity consists of the sequence of SEQ ID NO 4 and reacts with a racemic substrate selected from the group consisting of 2-chloro butyric acid, 2-fluoro butyric acid, 2-bromo-hexanoic acid and 2-bromo-4-methyl pentanoic acid.

Following the selective hydrolysis of the S-enantiomer of the chosen alpha haloalkanoic acid, the R-enantiomer and the hydrolyzed enantiomer are present as mixture. For some applications it is beneficial to only obtain i.e. purify the R-enantiomer. Hence, the mixture of R-enantiomer and the hydrolyzed enantiomer of the chosen alpha haloalkanoic acid according to Formula I is further processed.

A further aspect what is described herein relates to a use of the method described herein for the selective hydrolysis of the S-enantiomer of said alpha haloalkanoic acid, wherein the enantiomeric excess of the R-enantiomer is between 90.0 and 99.9.

It was surprisingly found that using a polypeptide with dehalogenase activity comprising an amino acid sequence as set forth in SEQ ID NO 1 or SEQ ID NO. 4 or a sequence with at least 80% sequence identity to either of said sequences for contacting a racemate comprising the R-enantiomer and the S-enantiomer of an alpha haloalkanoic acid according to formula I, wherein X is a halogen, in the case of SEQ ID NO 1 a halogen other than fluor, and R is a an alkyl chain containing up to 6 carbon atoms wherein that said alkyl chain can be straight or branched at carbon atoms γ or δ for 1-8 hours, wherein the pH is in the range of 9-10 and the temperature is in the range of 15-35° C. for the polypeptide comprising an amino acid sequence as set forth in SEQ ID NO. 1 or the pH is in the range of 9-10 and the temperature is in the range of 55-65° C. for the polypeptide comprising an amino acid sequence as set forth in SEQ ID No. 4 said polypeptide will carry out a selective hydrolysis of the S-enantiomer of said alpha haloalkanoic acid, wherein the enantiomeric excess of the R-enantiomer is between 90.0 and 99.9.

This result was unexpected since such high rates of enantiomeric excess are very unusual especially since the polypeptide with dehalogenase activity comprising the amino acid sequence as set forth in SEQ ID NO. 1 or SEQ ID NO 4 reaches enantiomeric excess values of 90-99 in the very short reaction time of 1-8 hours Hence, it was surprisingly found that via using the polypeptide with dehalogenase activity comprising an amino acid sequence as set forth in SEQ ID NO. 1 or SEQ ID NO 4 or a sequence with at least 80% sequence identity to said sequences with the described conditions allows for an alternative, safer and more cost effective and time-efficient method enabling and/or facilitating the separation of the R and S enantiomers of alpha haloalkanoic acids of Formula I based on differing reaction behavior of the two enantiomers with the polypeptide comprising an amino acid sequence as set forth in SEQ ID NO. 1 or SEQ ID NO 4 or a sequence with at least 80% sequence identity to either of said sequences.

In another aspect what is described herein relates to a method of selectively hydrolyzing an enantiomer of an alpha haloalkanoic acid according to formula II,

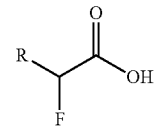

wherein
R is an alkyl chain of 1 to 6 carbon atoms, wherein that said alkyl chain can be straight or branched at carbon atoms γ or δ,
using a polypeptide having dehalogenase activity comprising an amino acid sequence as set forth in SEQ ID NO 4 or a sequence with at least 80% sequence identity to said sequence.

It was unexpectedly found that the polypeptide having dehalogenase activity comprising an amino acid sequence as set forth in SEQ ID NO 4 or a sequence with at least 80% sequence identity to said sequence selectively hydrolyses the S enantiomer of alpha haloalkanoic acids of Formula II, i.e. comprising a fluor atom, very efficiently and with a high enantiomeric excess.

Preferably, the above described method employing the polypeptide having dehalogenase activity comprising an amino acid sequence as set forth in SEQ ID NO 4 is carried out at 55-65° C. and at a pH of 9.5.

Thus, in the case of the polypeptide having dehalogenase activity comprising the amino acid sequence as set forth in SEQ ID NO 4 or a sequence with at least 80% sequence identity to said sequence in addition to the above named alpha haloalkanoic acids also 2-fluoro butyric acid is especially preferred.

In another aspect what is described herein relates to the use of the polypeptide having dehalogenase activity comprising an amino acid sequence as set forth in SEQ ID NO 4 or a sequence with at least 80% sequence identity to said sequence for the selective hydrolysis of the S-enantiomer of the alpha haloalkanoic acid of formula II, wherein the enantiomeric excess of the R-enantiomer is between 90.0 and 99.9.

In a preferred embodiment the method is carried out as follows the polypeptide with dehalogenase activity consisting of the amino acid sequence as set forth in SEQ ID NO. 1 is added to 2-Bromobutanoic acid at room temperature at a pH of 9.5. The reaction is allowed to proceed for 4-6 h, while the pH value is kept constant via titration with 3 M Potassium hydroxide.

In an especially preferred embodiment the method is carried out as follows 10 mg/ml of total cell protein as cell extract containing the polypeptide with dehalogenase activity consisting of the amino acid sequence as set forth in SEQ ID NO. 1 is added to 100 g/l 2-Bromobutanoic acid at room temperature, a pH of 9.5 and in a reaction volume of 6 L. The reaction is allowed to proceed for 4-6 h, while the pH value is kept constant via titration with 3 M Potassium hydroxide.

In another preferred embodiment the method is carried out as follows the polypeptide consisting of the amino acid sequence as set forth in SEQ ID NO. 4 is added to 2-Bromobutanoic acid at a temperature of 55° C., a pH of 9.5. The reaction is allowed to proceed for 4-6 h, while the pH value is kept constant via titration with 3 M Potassium hydroxide.

In a further especially preferred embodiment the method is carried out as follows 10 mg/ml of a total cell protein as cell extract containing of the polypeptide with dehalogenase activity consisting of the amino acid sequence as set forth in SEQ ID NO. 4 is added to 2-fluoro butyric acid at a temperature of 55° C., a pH of 9.5.

FIGURES

FIG. 1 shows a reaction carried out under optimized conditions with respect to pH value, i.e. 9.5 and temperature, i.e. 25° C. In this case 100 g/L 2-bromobutyric acid was used as substrate, 20 mM Glycine were present and 2 g/L cell lysate, i.e. E. coli MG1655 harbouring the pKA81a-HADH-PP-AJ plasmid were used to express the dehalogenase enzyme. The cell lysate was added 3 times, every hour.

Figure 2:
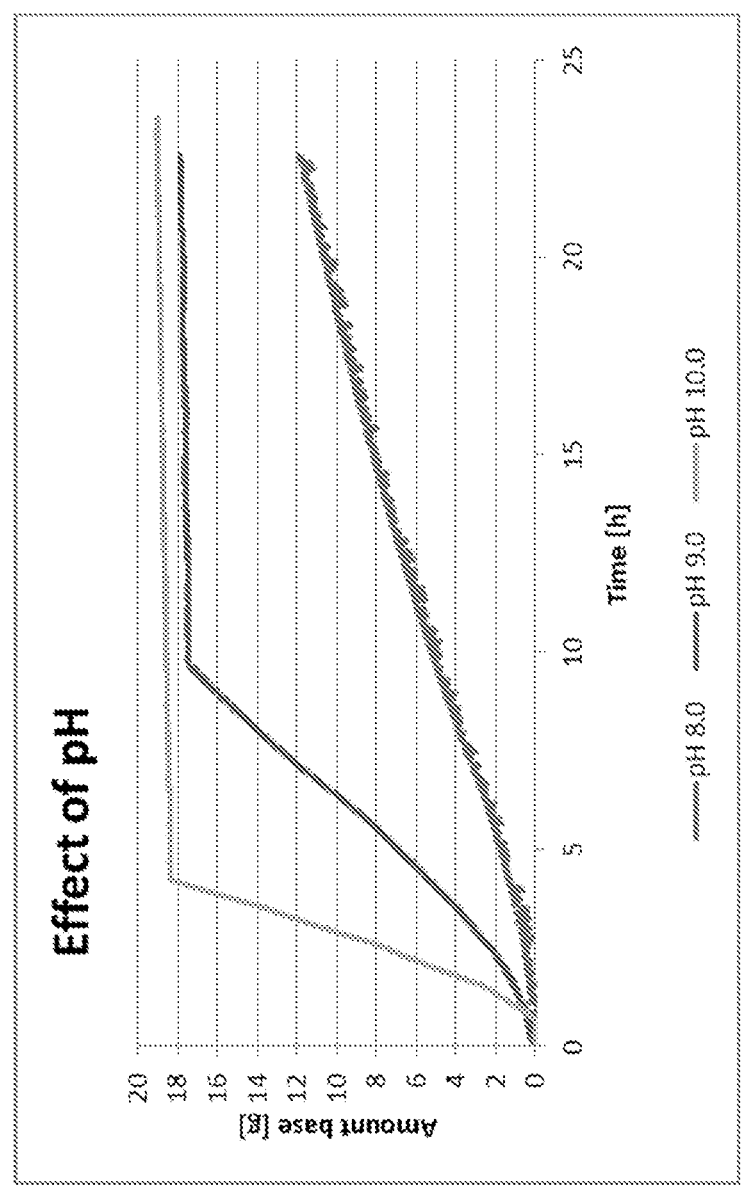

FIG. 2 demonstrates that the pH optimum of the reaction of FIG. 1 is between pH 8 and pH 10.

Figure 3:
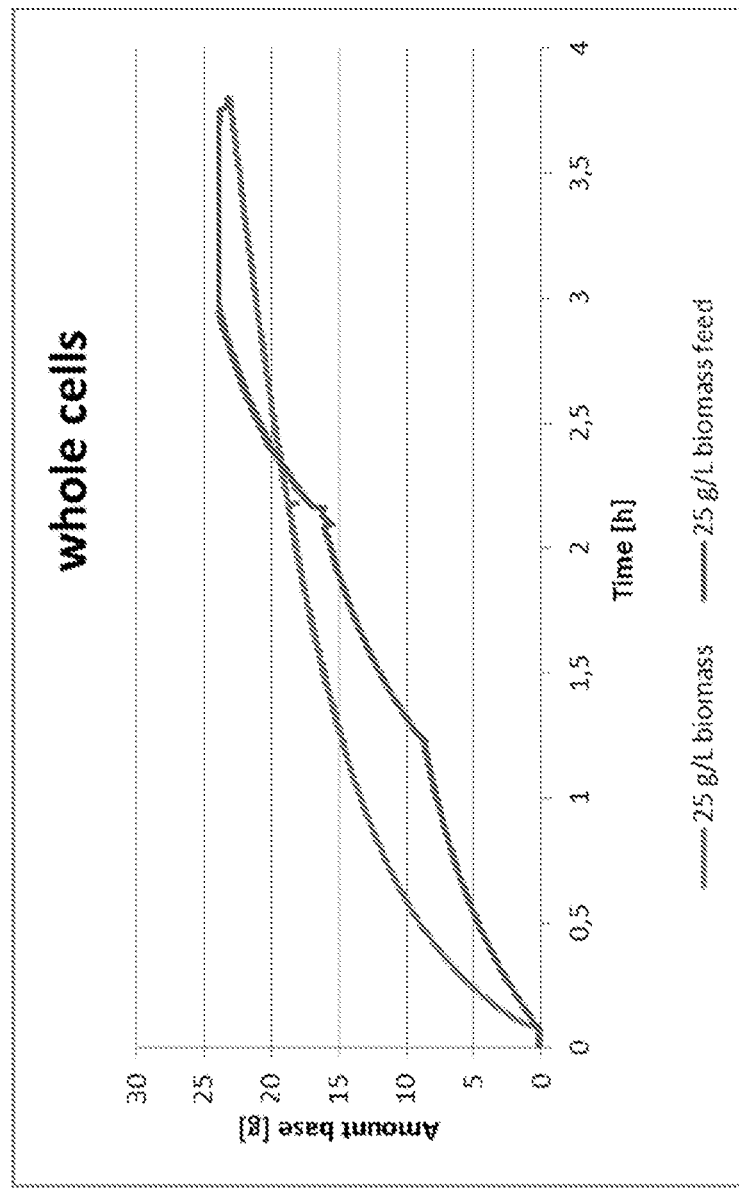
Figure 4:
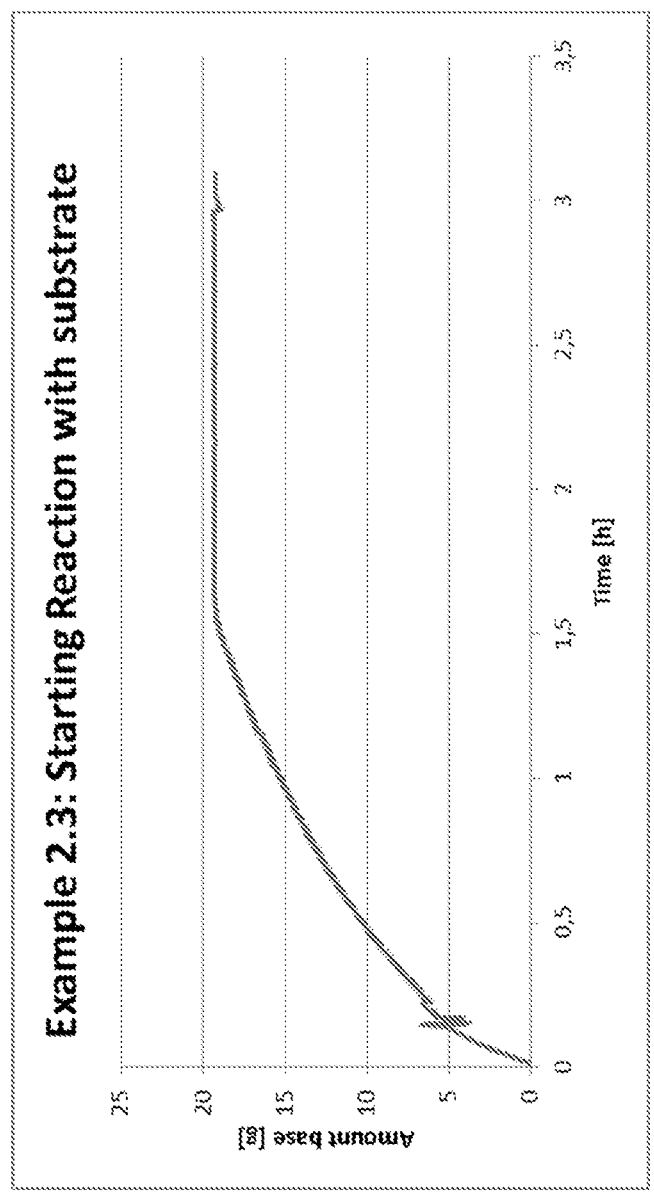

FIG. 3 demonstrates that instead of using (sterile) cell lysate also whole cells expressing the claimed enzyme can be used for the conversion reaction FIG. 4 demonstrates that the efficiency of the conversion reaction is maintained, if the substrate is provided and the enzyme is added to the substrate FIG. 5 demonstrates that the efficiency of the conversion reaction is maintained, if the enzyme is provided as fermentation broth and the substrate is added.

EXAMPLES

Example 1 Screening of Activity of Selected Haloacid Dehalogenase

Different haloacid dehalogenase from *P. putida* AJ, *P. putida* 109 and *S. tokodaii* 7 (Jones et al., 1992 (J Gen Microbiol. 1992 April; 138(4):675-83, Kawasaki et al., 1994 Biosci Biotechnol Biochem. 1994 January; 58(1):160-3 and Bachas-Daunert et al., 2009 Appl Biochem Biotechnol. 2009 November; 159(2):382-93) were cloned into *E. coli* MG1655 and overexpressed via IPTG treatment. 50 g/L 2-bromobutyric acid was used as substrate and 2×1.6 g/L cell lysate was added at the beginning of the reaction and after 3.5 h, while the pH was 9 and the temperature was set to 37° C.

The activity and stereoselectivity—i.e. the preferential hydrolysis of the S-enantiomer—was demonstrated for all three enzymes via analytics using gas chromatography with the enzyme from *P. putida* AJ (SEQ ID NO 1) showing the highest selectivity reaching an ee value of above 90%.

Example 2 Effect of pH on the Reaction Outcome

In order to test for the optimal pH range the reaction conditions were set to:

100 g/L 2-bromobutyric acid (substrate)
1.5 g/L cell lysate of *E. coli* expressing the *P. putida* AJ haloacid dehalogenase (SEQ ID NO 1) (6 times, every hour)
20 mM Glycine
Temperature: 25° C.
pH: kept constant at 8.0, 9.0, 10.0
As shown in FIG. 2 the best results are achieved with a pH of between 9-10.

Example 3: Further Optimization of the Selective Dehalogenation for Generation of High Enantiomer Excess Using the Haloacid Dehalogenase of *P. putida* AJ i.e. the Polypeptide Having Dehalogenase Activity Consisting of SEQ ID NO. 1

In a first case, 100 g/l rac-2-bromobutyric acid in 10 mM Glycine was used as substrate. The reaction was performed at 25° C. even though the optimal temperature for enzyme activity was at 37° C. since the substrate was more stable at 25° C. than at 37° C. and hence an autohydrolysis was prevented (data not shown)

The enzyme was provided as cell lysate and was added either all at the start of the reaction or every hour at a concentration of 2 mg/ml. The pH was kept constantly at 9.5 via titration with 3 M KOH until completion of reaction after approximately 4 hours. Subsequently, the pH was adjusted to pH 1.5 with concentrated $H_2SO_4$ and the cell debris was filtered over Celite. Extraction was performed with MTBE and washes to remove the remaining 2-Hydroxybutyric acid were carried out with aq. $CuSO_4$. Finally, concentration was performed in vacuo.

It was surprisingly found that the reaction reliably reached enantiomeric excess rate values of above 99% (data not shown).

These high enantiomeric excess rates i.e. the fact that after the reaction only the R-enantiomer of the alpha haloalkanoic acid and the hydroxylated product of the former S-enantiomer of the alpha haloalkanoic acid are present, render the process attractive for use on large industrial scale.

Example 4: Conversion with Whole Cells

Surprisingly, it was found that instead of preparing a cell lysate, whole cells could be used for the conversion. This has the advantage that the time-consuming step of preparing a (sterile) cell lysate can be omitted.

In a first case, racemic 2-bromo butyric acid at a concentration of 100 g/L was used as a substrate. The reaction parameters were set to 150 ml, 25° C., 500 rpm, 20 mM glycine buffer and pH 9.5. The pH was kept constant using 3 M KOH. The reaction vessel was prepared with the substrate mix and the reaction was started by addition of the enzyme, i.e. the addition of whole cells of *E. coli* MG1655 expressing the dehalogenase enzyme from *P. putida* AJ i.e. the polypeptide having dehalogenase activity consisting of SEQ ID NO. 1. The cells were added as either at the start of the reaction or stepwise after 1, 2, and 3 hours, at a concentration of 8.3 g/L respectively (cf. FIG. 3). The final concentration of the whole cells containing the enzyme was either 25 g/L or 50 g/L. The reaction was completed after 4 hours. The results presented in FIG. 3 and the table below demonstrate that ideally the reaction is carried out for more than 1 h hour e.g. for 4 hours.

| Sample | T[h] | % ee |
|---|---|---|
| 25 g/L biomass | 1 | 62 |
| 25 g/L biomass | 3 | 89 |
| 25 g/L biomass (feed) | 1 | 52 |
| 25 g/L biomass (feed) | 3 | 90 |

Subsequently, the reaction was repeated but the biomass consisting of the E coli MG1655 cells expressing the dehalogenase enzyme from P. putida AJ i.e. the polypeptide having dehalogenase activity consisting of SEQ ID NO. 1 was added to the reaction vessel before adding the substrate. The results are shown in FIG. 4 and the Table below. These results demonstrate that it is possible to first provide the enzyme as biomass comprising whole cells and to add the substrate to said biomass.

| t[h] | % ee |
|---|---|
| 1 | 61 |
| 2 | 78 |
| 3 | 88 |

Moreover, a conversion was performed using the fermentation broth. Again E. coli MG1655 harboring the pKA81a-HADH-PP-AJ plasmid were used to express the dehalogenase enzyme i.e. the polypeptide having dehalogenase activity consisting of SEQ ID NO. 1 Enzyme production was carried out by fermentation of E. coli in minimal medium using a standard protocol. After gene expression a cell concentration of 100 g/L was reached. The biotransformation was subsequently done with the untreated fermentation broth. The fermentation broth was cooled down to 25° C. and the pH was adjusted to 9.5 by adding 3 M KOH. The dehalogenase reaction was started by adding a substrate mix containing 100 g/L 2-bromobutyric acid, 0.5 Vol. (v/v) glycine buffer at pH 9.5 and 2 Vol (v/v) 5 M KOH. The reaction reached a full conversion i.e. 90% ee after 1 h (cf. FIG. 5).

From the resulting mix of hydroxybutyric acid and R-2-Bromobutyric acid around 30% pure R-2-Bromobutyric acid can be obtained using standard techniques such as acidification and extraction.

Example 5 Testing of Further Substrates

In addition to 2-bromobutyric acid further substrates were tested and the results are listed below

| | Substrates | | | | |
|---|---|---|---|---|---|
| Enzymes | 2-chloro-butyric acid | 2-fluoro-butyric acid | 2-bromo-hexanoic acid | 2-bromo-4-methyl-pentanoic acid | 2-bromo-3-cyclopropyl-propanoic acid |
| P. putida AJ SEQ ID NO. 1 | Yes | No | Yes; | Yes; | Yes; |
| P. putida 109 | Yes | No | No | Yes | Yes |
| S. sulfolobus SEQ ID NO. 4 | Yes | Yes | Yes | Yes | n.a.* |

Example 6: Upscaling

A prerequisite for the upscaling of the reaction to 2000 liters was the finding that the enzymes could be used comprised in whole cells which were provided as biomass without the need for preparing a cell lysate. Hence, time consuming and expensive preparation steps such as filtering the cell lysate, which are not economically feasible on large scale, could be omitted. Moreover, the finding that the reaction could be started either by addition of the substrate (racemate) or the biomass comprising the enzyme in whole cells meant that the equipment could be employed with a maximum flexibility. In order to further adapt the process the KOH used for pH titration (cf. above) was exchanged for 50% NaOH, the solvent for product extractions was changed from MTBE to MIBK and the CuSO4 used for removal of side products was exchanged for CaCl2 allowing for an easier and cheaper waste disposal.

The invention claimed is:

1. A method of selectively hydrolyzing the S-enantiomer of an alpha haloalkanoic acid according to formula I,

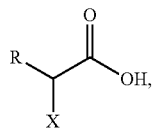

Formula I wherein X is bromide or chloride and
R is an alkyl chain of 1 to 6 carbon atoms, wherein said alkyl chain is straight or branched at carbon atoms γ or δ,
comprising:
providing a racemate of the R-enantiomer and the S-enantiomer of said alpha haloalkanoic acid,
providing a polypeptide having dehalogenase activity comprising the amino acid sequence as set forth in SEQ ID NO. 1,
reacting the racemate for 1-8 hours, wherein
the pH is in the range of 9-10 and the temperature is in the range of 15-35° C. for the polypeptide with dehalogenase activity comprising the amino acid sequence as set forth in SEQ ID NO. 1,
and wherein an enantiomeric excess of the R-enantiomer of the haloalkanoic acid of between 90.0% and 99.9% is reached after 1-8 hours, and wherein the concentration of the racemate of said alpha haloalkanoic acid according to Formula I is between 80 and 200 g/L and the polypeptide with dehalogenase activity is comprised within whole cells.

2. The method according to claim 1, wherein the ratio of racemate of the alpha haloalkanoic acid according to Formula I to biomass of whole cells comprising the polypeptide having dehalogenase activity comprising the amino acid sequence as set forth in SEQ ID NO. 1 or or a sequence with at least 90% sequence identity to said sequence is between 2:1 to 15:1.

3. The method according to claim 1, wherein moiety R of said alpha haloalkanoic acid of formula I is chosen from the group consisting of ethyl, butyl, 2-methyl-propyl and methyl-cyclopropyl.

4. The method according to claim 1 for selective hydrolysis of the S-enantiomer of an alpha haloalkanoic acid of formula I from a racemate, wherein the enantiomeric excess of the remaining R-enantiomer of said alpha haloalkanoic acid is between 90.0% and 99.9%.

5. A method of selectively hydrolyzing the S-enantiomer of an alpha haloalkanoic acid according to formula II,

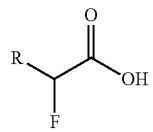

wherein
R is an alkyl chain of 1 to 6 carbon atoms, wherein said alkyl chain is straight or branched at carbon atoms γ or δ, and F is a single fluorine atom,
said method comprising:
providing a racemate of the R-enantiomer and the S-enantiomer of said alpha haloalkanoic acid,
providing a polypeptide having dehalogenase activity comprising the amino acid sequence as set forth in SEQ ID NO. 4,
reacting the racemate for 1-8 hours, wherein the pH is in the range of 9-10 and the temperature is in the range of 55-65° C. for the polypeptide with dehalogenase activity comprising the amino acid sequence as set forth in SEQ ID NO. 4,
wherein an enantiomeric excess of the R-enantiomer of the haloalkanoic acid of between 90.0% and 99.9% is reached after 1-8 hours, and
wherein the concentration of the racemate of said alpha haloalkanoic acid according to Formula II is between 80 and 200 g/L and the polypeptide with dehalogenase activity is comprised within whole cells.

6. The method according to claim 2, wherein the ratio is between 3:1 to 10:1.

7. The method according to claim 2, wherein the ratio is 4:1.

8. The method according to claim 1, wherein X is bromide.

9. The method according to claim 1, wherein X is chloride.

10. The method according to claim 3, wherein moiety R of said alpha haloalkanoic acid of formula I is ethyl.

11. The method according to claim 3, wherein moiety R of said alpha haloalkanoic acid of formula I is butyl.

12. The method according to claim 3, wherein moiety R of said alpha haloalkanoic acid of formula I is 2-methyl-propyl.

13. The method according to claim 3, wherein moiety R of said alpha haloalkanoic acid of formula I is methyl-cyclopropyl.

* * * * *